United States Patent
Nakanishi et al.

(10) Patent No.: US 6,511,816 B1
(45) Date of Patent: Jan. 28, 2003

(54) DNA GYRASE-INHIBITING PROTEINS

(75) Inventors: Akira Nakanishi, Tokyo (JP); Tadahiro Oshida, Tokyo (JP); Tadahiro Matsushita, Matsudo (JP); Tetsuo Onuki, Satte (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/306,454

(22) Filed: May 6, 1999

Related U.S. Application Data (63) Continuation-in-part of application No. PCT/JP97/04019, filed on Nov. 5, 1997, now abandoned.

(30) Foreign Application Priority Data

Nov. 6, 1996 (JP) ............................................. 8-293522

(51) Int. Cl.[7] ............................ C12Q 1/00; C12Q 1/34; C12N 9/00; C12N 9/14; C12N 9/16
(52) U.S. Cl. ............................ 435/18; 435/4; 435/183; 435/195; 435/196
(58) Field of Search ............................ 435/4, 183, 18, 435/195, 196

(56) References Cited

PUBLICATIONS

Baquero et al. 1995, Mol. Microbiol., vol. 18(2):301–311.*
GenBank Accession No. X84885, Dec. 19, 1995.*
GenBank Accession No. U00009, Feb. 17, 1994.*
GenBank Accession No. P33012, Feb. 1, 1994.*
Maki S. et al. J. Mol. Biol., Mar. 1996, vol. 256:473–482.*
M.R. Baquero et al., Molecular Microbiology 18(2), 301–311 (1995).
Baquero et al., *DNA Gyrase Inhibitory Protein (smbC protein)*, Swissprot Sequence DataBase, Feb. 1, 1994, XP002169018.
Baquero et al., *E. coli sbmC gene*, EMBL Sequence Database, Dec. 11, 1995, XP002169019.
Phillips et al., *sbcB region of E. coli K12 BHB2600*, EMBL Sequence Database, Nov. 27, 1993, XP002169020.
Maki et al., *Modulation of DNA supercoiling activity of Escherischia coli DnA gyrase by F plasmid proteins*, The Journal of Biological Chemistry, vol. 267, No. 17, Jun. 15, 1992, pp. 12244–12251, XP001002620.
Alami et al., *DNA gyrase inhibitory protein homolog (fragment)*, Swissprot Sequence DataBase, Nov. 1, 1995, XP002169021.
Alami et al., *Cloning and characterization of a gene cluster, phsBCdEF . . .* , Gene, vol. 156, 1995, pp. 53–57, XP004042386.
Murayama et al., *Evidence for Involvement of Escherichia coli Genes pmbA . . .* , Journal of Molecular Biology, vol. 256, 1996, pp. 483–502, XP002169022.

* cited by examiner

*Primary Examiner*—Rebecca E. Prouty
*Assistant Examiner*—Manjunath N. Rao
(74) *Attorney, Agent, or Firm*—Birch, Stewart, Kolasch & Birch, LLP

(57) ABSTRACT

The present invention discloses a protein that possesses an ability to inhibit bacterial DNA gyrase activity (DNA Gyrase-inhibiting protein; DGI); a host cell transformed by a replicable expression vector comprising a DNA that encodes DGI; a process for preparing DGI comprising culturing the same; a method for identifying a medical compound comprising assaying the action of modulating the DNA gyrase-inhibiting activity of DGI; and a method for identifying a medical compound comprising assaying the action of modulating the expression of a DGI-encoding gene.

7 Claims, 5 Drawing Sheets

Fig. 3 a : Fraction No. 32 Not added
b : Fraction No. 32 Added
c : Relaxed DNA
d : Supercoiled DNA

Fig. 4

Lane 1, 2 : E. coli (pCA18)
Lane 3, 4 : E. coli (pCA17)
Lane 5, 6 : E. coli (pLEX)
(Lane 1, 3 and 5 were induced by tryptophan)
Lane M (not shown) : Molecular weight marker (kDa)

Fig. 5

Lane 1 : 6 μg/ml of DGI added
Lane 2 : Control, No DGI added
Lane 3 : 3 μg/ml of DGI added
Lane 4 : 1.5 μg/ml of DGI added
Lane 5 : Control, No DGI added
Lane 6 : Supercoiled DNA
Lane 7 : Relaxed DNA

Fig. 6

Proliferation curve (pCA15: △, pCA16; ▲) of
E. coli JM109 (pCA15) and E. coli JM109 (pCA16)
and β-galactosidase activity (pCA15: ○, pCA16; ●)

Fig. 7

● ▲ No tryptophan added
○ △ Tryptophan added at the time = 0

Fig. 8

Lane 1 : Molecular weight marker (kDa)
Lane 2 : Cell extract, stained by CBB
Lane 3 : Cell extract, stained by anti-DGI antibody peroxidase

SEQUENCE LISTING

<160> NUMBER OF SEQ ID NOS: 9

<210> SEQ ID NO 1
<211> LENGTH: 16
<212> TYPE: PRT
<213> ORGANISM: Escherichia coli strain KL16

<400> SEQUENCE: 1

Met Asn Tyr Glu Ile Lys Gln Glu Glu Lys Arg Thr Val Ala Gly Phe
 1               5                   10                  15

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
ctggatccat cagcgggtag gggaaattga                                       30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
gtggatccca gactaacatc agcggtaacg                                       30

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
cacatatgaa ctacgagatt aagc                                             24

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
cacatatgag cgaaaaaatt gaaaggcg                                         28

<210> SEQ ID NO 6
<211> LENGTH: 1224
<212> TYPE: DNA
<213> ORGANISM: Escherichia coli strain KL16

<400> SEQUENCE: 6
ccatcagcgg gtaggggaaa ttgaacttta cgaccgtgat aaacaggtgg cgcactggcc      60
gctggttacc ctggaatctg tcggggaagg cagcatgttt tctcgcctga gtgattattt    120

-continued

| | |
|---|---|
| ccaccataag gcctgacctt tcttttgcag cagactggca ggagtgcgag tctgctcgca | 180 |
| taatcaacac tcattccttg tggttttaat tttgcaacta tactgtatat aaaaacagta | 240 |
| tcaatggagg cgtcatgaac tacgagatta agcaggaaga gaaacgtacc gttgcaggtt | 300 |
| tccatctcgt tggcccgtgg aacagacgg taaagaaagg ctttgagcag ttgatgatgt | 360 |
| gggtagatag caaaaatatt gtgccgaagg agtgggttgc tgtctattac gacaatccag | 420 |
| atgaaacacc cgccgaaaaa ttacgctgcg acaccgtcgt gacggtgccg ggttacttta | 480 |
| cgcttcccga aaacagtgag ggcgtcattc tgacagaaat acaggtggt cagtatgcgg | 540 |
| tggcggtagc tcgtgtagtc ggtgatgatt ttgctaaacc ctggtatcag ttctttaata | 600 |
| gtctcttgca ggacagtgct tatgaaatgt taccaaagcc ctgcttcgag gtttatttga | 660 |
| acaatggcgc ggaagatggg tactgggata tcgaaatgta tgttgcggtg cagccaaaac | 720 |
| atcactaatt catctcaggg cggtgtgtta acgcgatgac cactcttttt tttgaaagcg | 780 |
| aaaagagtaa gatgcgcctt tcaatttttt cgctcctgcc gggaaattac actgttcccg | 840 |
| gtttgtccgt cggataattc agaggcgcgc cttctggccg acagatgagt tatgagcgct | 900 |
| tttaatctca ttacggagtt tctgcgtgcg tgccgataag tcattaagcc cgtttgaaat | 960 |
| ccgggtatac cgccattacc gcattgtgca tggtactcgg gtcgcgctgg cattcctgct | 1020 |
| cactttctc attatccgcc tgtttactat cccggaaagc acctggccgc tggtcaccat | 1080 |
| ggtggtgatt atgggccaa tctcgttctg gggtaacgtt gtccctcgcg cctttgagcg | 1140 |
| tattggcggt acggtgttgg gttcgatttt aggtcttatc gctctgcaac tggagttaat | 1200 |
| ctcgttaccg ctgatgttag tctg | 1224 |

<210> SEQ ID NO 7
<211> LENGTH: 157
<212> TYPE: PRT
<213> ORGANISM: Escherichia coli strain KL16

<400> SEQUENCE: 7

Met Asn Tyr Glu Ile Lys Gln Glu Glu Lys Arg Thr Val Ala Gly Phe
 1               5                  10                  15

His Leu Val Gly Pro Trp Glu Gln Thr Val Lys Lys Gly Phe Glu Gln
            20                  25                  30

Leu Met Met Trp Val Asp Ser Lys Asn Ile Val Pro Lys Glu Trp Val
        35                  40                  45

Ala Val Tyr Tyr Asp Asn Pro Asp Glu Thr Pro Ala Glu Lys Leu Arg
    50                  55                  60

Cys Asp Thr Val Val Thr Val Pro Gly Tyr Phe Thr Leu Pro Glu Asn
65                  70                  75                  80

Ser Glu Gly Val Ile Leu Thr Glu Ile Thr Gly Gly Gln Tyr Ala Val
                85                  90                  95

Ala Val Ala Arg Val Val Gly Asp Asp Phe Ala Lys Pro Trp Tyr Gln
            100                 105                 110

Phe Phe Asn Ser Leu Leu Gln Asp Ser Ala Tyr Glu Met Leu Pro Lys
        115                 120                 125

Pro Cys Phe Glu Val Tyr Leu Asn Asn Gly Ala Glu Asp Gly Tyr Trp
    130                 135                 140

Asp Ile Glu Met Tyr Val Ala Val Gln Pro Lys His His
145                 150                 155

<210> SEQ ID NO 8
<211> LENGTH: 1444

```
<212> TYPE: DNA
<213> ORGANISM: Shigella dysenteriae strain IID633

<400> SEQUENCE: 8
ccgagtttta tcatatgtac agtgagaaaa gtctcacctg gaacggtatc acccagcaaa      60
accgtaacgg gttattgtgg gataaaacca tgaatgttga cggcctgaaa acgggtcata     120
cttctggtgc cgggtttaat ctcattgctt cggctgtcga tgggcagcgt cgtctcattg     180
cagtggtaat gggggctgac agtgcaaaag gtcgtgagga agaggcaaga aaattactgc     240
gttgggggca acaaaacttt actacggtgc aaattttgca ccgtgggaaa aaggtcggta     300
cggaacgcat ctggtatggc gataaagaaa atatcgacct gggaacggaa caagagttct     360
ggatggtgct accgaaagcc gaaattccac atatcaaagc caaatatacc cttgatggta     420
aagagctcac cgcgccaatt agcgcccatc agcgggtagg ggaaattgaa ctttacgacc     480
gtgataaaca ggtggcgcac tggccgctgg ttaccctgga atctgtcggg gaaggcagca     540
tgttttctcg cctgagtgat tatttccacc ataaggcctg acctttcttt tgcagcagac     600
tggcaggagt gcgagtctgc tcgcataatc aacactcatt ccttgtggtt ttaatatcgc     660
aattatactg tatataaaaa cagtgttgat ggagcgtcat gaactacgag attaagcagg     720
aagataaacg taccgttgca ggtttccatc tcgttggccc gtgggaacag acggtaaaga     780
aaggctttga gcagttgatg atgtgggtag atagcaaaaa tattgtgccg aaggagtggg     840
ttgctgtctt ttacgacaat ccagatgaaa cacccgccga aaaattacgc tgcgacaccg     900
tcgtgacggt gccgaataac tttacgctcc ccgaaaacag tgagggcgtc attctgacag     960
aaatttcagg tggtcagtat gcggttgcgg tggctcgtgt agtcggtgat gattttgcta    1020
aaccctggta tcagttcttt aatagcctct tgcaggacag tgcttatgaa atgttaccaa    1080
agccctgctt cgaggtttat ttgaacaatg gcgcggaaga tgggtactgg gatatcgaaa    1140
tgtatgttgc ggtgcagcca aaacatcact aattcatctc agggcggtgt gttaacgcga    1200
tgaccactct ttttttgaaa gcgaaaagag taagatgcgc ctttcaattt tttcgctcct    1260
gccgggaaat tacactgttc ccggtttgtc cgtcggataa ttcagaggcg ggccttctgg    1320
ccgacagatg agttatgagc gcttttaatc ttcattacgg agtttctgcg tgcgtgccga    1380
taagtcatta agcccgtttg aaatccgggt ataccgccat taccgcattg tgcatggtac    1440
tcgg                                                                 1444
```

<210> SEQ ID NO 9
<211> LENGTH: 157
<212> TYPE: PRT
<213> ORGANISM: Shigella dysenteriae strain IID633

<400> SEQUENCE: 9

```
Met Asn Tyr Glu Ile Lys Gln Glu Asp Lys Arg Thr Val Ala Gly Phe
  1               5                  10                  15

His Leu Val Gly Pro Trp Glu Gln Thr Val Lys Lys Gly Phe Glu Gln
             20                  25                  30

Leu Met Met Trp Val Asp Ser Lys Asn Ile Val Pro Lys Glu Trp Val
         35                  40                  45

Ala Val Phe Tyr Asp Asn Pro Asp Glu Thr Pro Ala Glu Lys Leu Arg
     50                  55                  60

Cys Asp Thr Val Val Thr Val Pro Asn Asn Phe Thr Leu Pro Glu Asn
 65                  70                  75                  80

Ser Glu Gly Val Ile Leu Thr Glu Ile Ser Gly Gly Gln Tyr Ala Val
```

-continued

```
                        85                      90                      95
Ala Val Ala Arg Val Val Gly Asp Asp Phe Ala Lys Pro Trp Tyr Gln
                100                 105                 110

Phe Phe Asn Ser Leu Leu Gln Asp Ser Ala Tyr Glu Met Leu Pro Lys
        115                 120                 125

Pro Cys Phe Glu Val Tyr Leu Asn Asn Gly Ala Glu Asp Gly Tyr Trp
        130                 135                 140

Asp Ile Glu Met Tyr Val Ala Val Gln Pro Lys His His
145                 150                 155
```

DNA GYRASE-INHIBITING PROTEINS

This is a continuation-in-part application of PCT/JP97/04019 filed on Nov. 5, 1997 claiming a priority of Japanese Patent Application No. 293522/1996 of Nov. 6, 1996 now abandoned.

TECHNICAL FIELD

This invention relates to a protein which inhibits bacterial DNA gyrase activity (DGI) and to a process for the preparation thereof. This invention further relates to a method for screening and identifying an antimicrobial agent and the like, by assaying the action of compounds on the activity or expression of DGI. Furthermore, this invention relates to an antisense DNA (or RNA) of a gene which encodes DGI and an antibody to DGI.

BACKGROUND ART

Since penicillin had been discovered, various antibiotics have been used for treating microbe infections and have a great contribution to medical treatments. Major antibiotics which have been used presently in clinical treatments are β-lactam antibiotics and new quinolone antibiotics. The action and mechanism of new quinolone antibiotics are found to be the inhibition of bacterial DNA gyrase.

Bacterial DNA gyrase is an essential enzyme for replication and proliferation of bacteria, since the gyrase introduces a negative supercoiled structure into chromosomal DNA, or unravels and separates tangled daughter DNA just after completion of replication, and it is constituted of two subunits (A and B).

As DNA gyrase inhibitors, compounds such as novobiocin and cyclothiazine are known in addition to new quinolone antibiotics, but proteinous inhibitors have not been known.

Regarding the control of DNA gyrase activity, Horiuchi et al. have reported that LetD and LetA proteins encoded on the F factor which is a plasmid of *Escherichia coli* are involved in inactivation of DNA gyrase and reactivation of inactive gyrase, respectively (Journal of Biological Chemistry, vol. 267, pp. 12244–12251, 1992). However, inactivation with LetD protein is found only in experiments using the whole of microbial cells, and the inactivation action is not recognized in in vitro reconstitution experiments. Further, there is no report on DNA gyrase-inhibiting proteins encoded on a bacterial chromosome.

Recently, the appearance of bacteria tolerant against the conventional β-lactam or new quinolone antibiotics becomes a serious problem and antibiotics with new action and mechanism which have efficacy to these tolerant bacteria have been desired.

An object of the present invention is to provide a DNA gyrase-inhibiting protein (DGI) useful for the creation of antibiotics with new action and mechanism and a process for preparing the same. Further, another object is to provide a method for screening and identifying an antimicrobial agent with new action and mechanism in which the activity of DGI and expression thereof are modulated using DGI or a gene therefor.

The present inventors have found that, when the supercoiling activity of each fraction is measured and each fraction is analyzed with SDS-polyacrylamide electrophoresis in the course of carrying out the purification of *Escherichia coli* DNA gyrase using novobiocin-affinity column chromatography, there are present fractions which contain a holoenzyme of DNA gyrase, but they do not show the supercoiling activity and these fractions contain a protein with about 18 kDa in common. The present inventors have found the absolutely new finding that the about 18 kDa protein has the action of inhibiting the DNA gyrase activity (supercoiling activity), and named the 18 kDa protein "DNA gyrase-inhibiting protein" (DGI) (also referred to as GyrI). Further, the present inventors have cloned a gene encoding this protein (dgi gene) (also referred to as gyrI gene) from the chromosome of *Escherichia coli* to establish a process for preparing DGI. The present inventors have further constructed a system for measuring DGI activity using purified DGI, and a system for measuring expression of DGI using a promoter region of the dgi gene. Furthermore, the present inventors have found that the growth of bacteria can be controlled by modulating the activity or expression of DGI and thereby accomplished the invention.

DISCLOSURE OF THE INVENTION

The present invention relates to a protein which inhibits the activity of bacterial DNA gyrase (DNA gyrase-inhibiting protein; DGI).

Further, the present invention relates to a host cell transformed by a replicable expression vector which contains a DGI-encoding DNA, and to a process for preparing DGI comprising culturing the host cell.

The present invention also relates to a process for identifying a medical compound comprising assaying the action of modulating DNA gyrase-inhibiting activity that DGI has, and to a process for identifying a medical compound characterized by assaying the action of modulating the expression of a DGI-encoding gene.

Furthermore, the present invention relates to an antisense DNA or an antisense RNA of a DGI-encoding gene, and to a DGI-recognizing antibody.

BEST MODE FOR PRACTICING INVENTION

Sequence ID NO:1 of Sequence listing set forth hereinafter shows the amino acid sequence of the N-terminus (16 residues) of DGI derived from *Escherichia coli*, Sequence ID NOs:2 and 3 show the base sequences of synthetic primer DNAs used for cloning the dgi gene encoding for *Escherichia coli* DGI, Sequence ID NOs:4 and 5 show the base sequences of synthetic primer DNAs used for preparing an expression vector for *Escherchia coli* DGI, Sequence ID NO:6 shows the base sequence of a DNA fragment containing an *Escherichia coli* dgi gene and the amino acid sequence of DGI encoded therein and Sequence ID NO:7 shows the amino acid sequence of *Escherchia coli* DGI, respectively. Sequence ID NO:8 represents the base sequence of a DNA fragment containing dgi gene derived from a microorganism of Shigella genus and the amino acid sequence of DGI encoded therein, and Sequence ID NO:9 represents the amino acid sequence of DGI derived from a microorganism of Shigella genus, respectively.

As a bacterium that produces DGI of the invention, *Escherichia coli* can be suitably used. Specific strains may include *Escherichia coli* KL16 strain (National Institute of Genetics, Genetic Strain Research Center, Accession No. ME8002), ditto K-12 strain (Genetics, vol. 38, pp. 51–64, 1953), ditto ML1410 (Microbiology and Immunology, vol. 22, pp. 367–375, 1978), ditto ATCC25922, ditto NIHJ JC-2, ditto JM109 strain (ATCC 53323), ditto GI724 (Invitrogen Co., USA) and so on.

DGI of the present invention is also present widely and universally in various bacteria other than *E. coli,* and examples of such bacteria may include microorganisms belonging to Shigella genus, Citrobacter genus, Pseudomonas genus, Bacillus genus, Enterococcus genus and Staphylococcus genus. Specific examples of strains include *Shigella boydii* IID627 (NIHJ 1130 Type 7)(Japanese Journal of Bacteriology, vol. 50, pp. 1019–1031, 1995, Table 1-1), ditto ATCC35964, ditto ATCC49348, *Shigella dysenteriae* IID633 (NIHJ 177249 Type 3) (Japanese Journal of Bacteriology, vol. 50, pp. 1019–1031, 1995, Table 1-1), ditto ATCC13313, ditto ATCC23351, ditto ATCC49345, *Shigella sonnei* TRRL10805, ditto ATCC11060, ditto ATCC29930, *Citrobacter freundii* IID976 (NIH 17), *Pseudomonas aeruginosa* ATCC27853, *Bacillus subtilis* ATCC6633, *Enterococcus faecalis* ATCC29212, *Staphylococcus aureus* RN450 (Journal of Bacteriology, vol. 174, pp. 4952–4959, 1992) and so on.

Purification of DGI can be carried out from a bacterial culture by variously combining purification procedures, such as ammonium sulfate precipitation, affinity chromatography, ion exchange chromatography and gel filtration chromatography using its physiological activity (the action of inhibiting the supercoiling activity of DNA gyrase) as an index, e.g. as shown below.

When the nature that DGI is present in combined form with DNA gyrase is utilized, for example, nucleic acid removal, ammonium sulfate precipitation and fractionation using a novobiocin-affinity column are carried out from an extracted liquid from microbial cells in the logarithmic growth phase, according to the DNA gyrase-purifying method (Aoyama et al., Antimicrobial Agents and Chemotherapy, vol. 32, pp. 104–109, 1988). Since novobiocin bonds to DNA gyrase, novobiocin-affinity chromatography is used for fractionation and purification of DNA gyrase. For each fraction, the supercoiling activity of DNA gyrase is measured and SDS-polyacrylamide gel electrophoresis is carried out, and fractions are collected in which the presence of a protein corresponding to a DNA gyrase holoenzyme is confirmed by the SDS-polyacrylamide gel electrophoresis but which do not show supercoiling activity, namely in which DNA gyrase is coexistent with DGI. DGI can be-isolated and purified from the fractions by gel filtration using Sephadex G-75 and the like.

Alternatively, using an extracted liquid from microbial cells in the logarithmic growth phase, DGI can be also purified by ammonium sulfate precipitation, strong anion exchange chromatography using Q-Sepharose fast flow column (Pharmacia Co.), gel filtration using TSK gel Toyopearl HW-55 column (Toso Co.) and SDS polyacrylamide electrophoresis.

The supercoiling activity of DNA gyrase can be measured in accordance with, e.g. the procedure described in Antimicrobial Agents and Chemotherapy, vol. 32, pp. 104–109, 1988. The DGI activity, namely the action of inhibiting the supercoiling activity of DNA gyrase, can be measured utilizing the supercoiling activity measurement system.

The purified DGI derived from *Escherchia coli* was a protein having a molecular weight of about 18 kDa. And, the amino acid sequence of its N-terminus is represented by Sequence ID NO:1 set forth hereinbelow.

The homology search using a nucleic acid sequence data bank (EMBL/Genbank/DDBJ) indicated that the N-terminal sequence of DGI was identical with the N-terminal amino acid sequence of an assumed product (hypothetical protein) YeeB in the sbcB region (EMBL Accession No. U00009) of chromosomal DNA of *Escherchia coli* K-12 strain. In addition, the molecular weight of DGI corresponded to that of the hypothetical protein YeeB. From the above-mentioned facts, the inventors believed that YeeB was DGI and a DGI-encoding gene (dgi gene) was present in a part containing the translational region of YeeB and the inventors thus have cloned the *Escherchia coli* dgi gene based on the base sequence before and behind the translational region of yeeB gene.

EMBL Accession No. U00009 describes the base sequence of the sbcb region of chromosomal DNA of *Escherchia coli* K-12 strain, and the amino acid primary sequence of a structural gene product supposed from the base sequence by the person entitled the registration. However, physiological activity and functions of such hypothetical products (such as YeeB and the like), which are most important information, are not at all known or suggested therein, and it is not even known whether or not the hypothetical products are really expressed in a cell. Further, the sbmC gene (gene product SbmC) is reported which is present in the sbcB region and has the same sequence as the yeeB (EMBL Accession No. X84885 and Molecular Microbiology, vol. 18, pp. 301–311, 1995). However, regarding the sbmC gene, there are some descriptions on the relation with the tolerance against a peptidious antibiotic substance Microcin B17 and on the supposition that it is one of SOS genes, but it is still not disclosed what physiological activity and function the gene product has.

The dgi gene of *Escherchia coli* can be cloned by carrying out polymerase chain reaction (PCR) with *Escherichia coil* chromosomal DNA as a template using a primer which is designed and synthesized on the basis of the base sequence before and behind the yeeB translational region of the above-mentioned sbcB region (EMBL Accession No. U00009). After optional cleavage with a suitable restriction enzyme, PCR products may be ligated to a vector plasmid which is replicable in the *Escherchia coli* host.

A dgi gene derived from *Escherchia coli* or a bacterium other than *Escherchia coli* can be easily cloned, for example, by preparing the library of a desired bacterial chromosomal DNA and screening it using a labeled DNA fragment containing part or all of the *Escherichia coli* dgi gene as a probe. For instance, it can be done by using as a probe a DNA fragment of dgi gene comprising the base sequence shown in Sequence ID NO:6 or Sequence ID NO:8 and selecting genes which hybridizes with the fragment in stringent conditions. The DNA base sequence of the positive clones thus obtained is determined, and thereby the DNA sequence of dgi gene can be determined and from its translational region, the amino acid sequence of DGI can be obtained. Such dgi genes derived from bacteria other than *Escherchia coli* generally have a homology of 70% or more, preferably 80% or more, more preferably 90% or more in the base sequence.

DNA libraries may be prepared by, for example, the method described in "Molecular Cloning" (written by Sambrook, J., Fritsch, E. F. and Maniatis, T., published by Cold Spring Harbor Laboratory Press in 1989). Alternatively, if there are present commercially available libraries, these may be used.

DGI may be expressed in a host cell by gene recombination techniques using a DGI-encoding DNA, such as dgi gene. An expression plasmid is constructed by connecting a DGI-encoding DNA to the downstream of a suitable promoter (e.g. λpL promoter, trp promoter, lac promoter or T7 promoter if *Escherchia coli* is used as a host), and inserting it into a vector capable of functioning in a host microorganism (e.g. pBR322, pUC18 or pUC19 if *Escherchia coli* is used as a host). Alternatively, a DGI-encoding DNA may be ligated to an expression vector containing a suitable promoter. Since normal growth of a host cell is repressed when a large amount of DGI is expressed, it is preferable to use a vector containing a promoter capable of controlling expression induction in order to express large amounts of DGI, which expression vector may include pLEX (available from Invitrogen Co.) and pET (available from Novagen Co.) if *Escherchia coli* is used as a host.

A host cell transformed with the thus obtained expression vector (i.e. a replicable expression vector containing a DGI-encoding DNA) is cultured and the desired DGI can be prepared from the culture broth or microbial cells thus obtained.

As a DGI-encoding DNA, there may be used a naturally occurring gene of a microorganism but it is not limited thereto. For instance, any DNA encoding the amino acid sequence shown by Sequence ID NO:7 may be used in the case of *Escherchia coli* DGI while any DNA encoding the amino acid sequence shown by Sequence ID NO:9 may be used in the case of DGI of a microorganism of Shigella genus. A codon corresponding to each amino acid is known, and thus a DNA can be designed corresponding to an amino acid sequence and it can be used as a polypeptide-encoding DNA, without limiting to any native dgi genes. One to six codons are known to encode each amino acid and any one of these codons can be selected optionally; for example, a sequence with higher expression efficacy may be designed in consideration of frequency in use of codons of a host used for expression. A DNA with a designed base sequence may be obtained by, e.g., chemical synthesis or partial modification of a naturally occurring gene. Artificial partial modification of a base sequence and introduction thereinto of mutation can be carried out by the known site-specific mutation introducing method (Mark, D. F. et al., Proceedings of National Academy of Sciences, vol. 81, pp. 5662–5666 (1984)) using as a primer a synthetic oligonucleotide encoding a desired modification.

In *Escherchia coli* in which a large quantity of DGI is expressed, abnormal cell division may be seen. And, if the DGI expression is repressed by expressing an antisense RNA of dgi gene, elongation of a bacterium can be seen and such abnormality in morphology is also observed when *Escherichia coli* is treated with a new quinolone agent which is a gyrase inhibitor (Takeshi Nishino et al., Chemotherapy, 41(s-5), 50–66, 1993). From these, a medical compound which modulates (increases or inhibits) the DGI activity or modulates (increases or inhibits) the expression of dgi gene is considered to be useful for antimicrobial agents.

Using the DGI of the present invention, a compound to be tested can be assayed as to whether or not it has the action to modulate the DGI activity (DNA gyrase-inhibiting activity). Furthermore, a compound to be tested can be assayed as to whether or not it has the action of modulating the expression of dgi gene, using a promoter of the dgi gene of the present invention. By such assays, for example, a medical compound useful for an antimicrobial agent can be screened and identified.

As the method for effectively assaying as to whether or not a compound to be tested has the action to modulate the DGI activity using a promoter of the dgi gene of the present invention, there is exemplified a method comprising the use of a recombinant plasmid which is obtained by ligating an indicator gene to the downstream of a promoter region in the dgi gene and which is designed to express the indicator gene in the control of the promoter of the dgi gene. The promoter activity is efficiently measured using as an index the expression of an indicator protein in a transformed host cell by transforming the host cell with the thus obtained recombinant plasmid. There is present the problem between the heterogeneous species that the expression efficiency is different, and therefore a microorganism to be used as a host and the source of a dgi promoter are preferably homogeneous. As indicator proteins (indicator genes), there are exemplified β-galactosidase (lacZ gene), luciferase (luc gene) and alkali phosphatase (phoA gene).

Substances to modulate expression of the dgi gene may include, for example, an antisense DNA or RNA of the dgi gene. Such DNA or RNA may be obtained by chemical synthesis and the like. Also, an antisense RNA can be obtained by expressing a plasmid in a host wherein a fragment containing part of the gene is inserted into an expression vector in a reverse direction (in an antisense direction).

Further, an antibody (monoclonal or polyclonal antibody) which specifically recognizes the DGI can be obtained using a purified DGI. For example, polyclonal antibodies may be obtained by the conventional method, such as a method comprising inoculating a suitable host animal (such as a rabbit or mouse) with a purified DGI, its fragment or a synthetic peptide containing a partial sequence thereof, and collecting antiserum. Monoclonal antibodies can be prepared by technical procedures, such as the conventional hybridoma methods, using purified DGI, its fragment or a synthetic peptide containing a partial sequence thereof as an antigen. The thus obtained antibody may be used, for example, for detecting, quantifying or purifying the DGI.

The DGI of the present invention may include its fragments and their homologues. Such fragments or homologues may be any material so long as it has either biological activity similar to that of DGI (of substantially the same type and efficacy as the DGI), or immunological equality thereto. More specifically, as DGIs, there are exemplified, in addition to those comprising the amino acid sequence shown by Sequence ID NO:7 or 9, those comprising an amino acid sequence wherein one or several amino acids are deleted, substituted or added in the amino acid sequence shown by Sequence ID NO:7 or 9. The degree of deletion, substitution or addition of amino acids may be such that the potency to inhibit the DNA gyrase activity is not lost, and generally 1 to about 30, preferably 1 to about 15, more preferably 1 to about 7 are applied thereto. Such proteins have a homology of normally 80% or more, preferably 90% or more, more preferably 95% or more to the amino acid sequence represented by Sequence ID NO:7 or 9.

As genes encoding the DGI of the present invention, there are exemplified, in addition to DNAs comprising the base sequence represented by Sequence ID NO:6 or 8, those capable of hybridizing with a DNA comprising the base sequence represented by Sequence ID NO:6 or 8 under stringent conditions. Any one of such hybridizable DNAs may be one having the potency that a protein encoded by the DNA inhibits the DNA gyrase activity. Such DNAs have a base sequence homology of normally 70% or more, preferably 80% or more, more preferably 90% or more to the base sequence represented by Sequence ID NO:6 or 8. These DNAs may include mutated genes naturally found, artificially modified mutated genes and homologous genes derived from heterogeneous organisms.

The hybridization under stringent conditions in the present invention can be carried out in such a manner that hybridization is applied to a hybridization solution with 5×SSPE (5 times the concentration of SSPE) or an equal salt concentration thereto under the temperature condition of 37 to 42° C. for about 12 to 18 hours, prewashing is carried out, if necessary, in 5×SSPE or a solution with an equal salt concentration thereto, and washing is carried out in 1×SSPE or a solution with an equal salt concentration thereto under the temperature condition of 50 to 65° C. In order to obtain higher stringency, washing is carried out in a solution with a lower salt concentration, such as 0.1 ×SSPE or a solution with an equal salt concentration thereto.

The present invention is explained in more detail with Examples below but these Examples do not limit the scope of the present invention.

In the following Examples, each procedure, when not specifically illustrated otherwise, was done according to the method described in "Molecular Cloning" (written by Sambrook, J., Fritsch, E. F. and Maniatis, T. and published by Cold Spring Harbor Laboratory Press in 1989), or when commercially available regents or kits were used, they were applied under the instructions therefor.

EXAMPLES

Example 1

Isolation and Identification of *Escherichia coli* DNA Gyrase-inhibiting Protein (DGI)

(1) Culture of Bacterium

Using *Escherichia coli* KL 16 strain as a strain, culturing was carried out as below. In 1000 ml of pure water were dissolved 1 g of $(NH_4)_2SO_4$, 3 g of $KH_2PO_4$, 5.25 g of $K_2HPO_4$, 0.57 g of sodium citrate dihydrate and 0.12 g of $MgSO_4$ and after sterilization, a separately sterilized casein hydrolysate and glucose were added thereto such that the concentration thereof became 1% to prepare a culture medium. 150 ml of this medium was introduced into an Erlenmeyer flask of 500 ml volume and 10 ml of the cultured medium (cultured overnight) was added thereto to carry out rotation and shaking (160 rpm) at 37° C. Culture medium in the late logarithmic growth phase (about 1.0 of OD600) was rapidly cooled and thereafter centrifuged (5000 rpm×10 min) at 4° C. to collect the cells. It was washed twice with a TED buffer (10 mM Tris-HCl (pH 7.5), 1 mM EDTA and 1 mM dithiothreitol) and it was, after measurement of the wet weight, suspended in an equal volume of the TED buffer and was apportioned to each about 20 ml and preserved at −80° C.

(2) Purification of *Escherichia Coli* DNA Gyrase

The purification of DNA gyrase was carried out in accordance with the method of Aoyama et al. (Antimicrobial Agents and Chemotherapy, vol. 32, pp. 104–109, 1989) as follows.

The bacterial cell preserved at −80° C. was thawed at room temperature and 0.5 ml of 0.5M dithiothreitol, 2 ml of 0.5M EDTA, 4 ml of 0.5M KCl and 2 ml of a lysozyme solution at 30 mg/ml were added successively per 20 ml thereof to perform slow shaking at room temperature for 15 minutes. Thereafter, Brij 58 (available from Sigma Co.) was added to 0.5% concentration and agitation was carried out in ice for 30 minutes. The reaction mixture was ultracentrifuged (35,000 rpm×1 hour) at 4° C. and a supernatant was separated. To the supernatant was added 20% streptomycin to the final concentration of 2% and nucleic acids were removed. Thereafter, agitation was carried out for 30 minutes in ice and centrifugation (12,000 rpm×15 min) was carried out at 4° C. to obtain a supernatant. 0.39 g of ammonium sulfate was added per ml of the supernatant and was centrifuged (12,000 rpm×20 min) to obtain a precipitate. The precipitate was suspended in 20 ml of a TED buffer and thereafter dialyzed in 4000 ml of a TED buffer at 4° C. to obtain a crude extract (50 ml). The crude extract was loaded on a novobiocin-Sepharose column (bed volume 30 ml) which had been previously equilibrated with a TED buffer. The novobiocin-Sepharose column was used which had been prepared by coupling novobiocin (available from Sigma Co.) to epoxy-activated Sepharose 6B (available from Pharmacia Co.) according to the method of Staudenbauer & Orr et al. (Nucleic Acids Research, vol. 9, pp. 3589–3603, 1989). After washing the column with 6 times the volume of a TED buffer, it was eluted successively with TED buffers containing each of 0.2M KCl, 2M KCl, 5M urea, 2M KCl-5M urea and 2M KCl-5M urea (pH 4.0) and fractionated. Each 3 ml of the fractions of the eluent was dialyzed in a TED buffer-50% glycerin at 4° C. overnight and thereafter the supercoiling activity of each fraction was measured by the method described in Reference Examples below.

Figure 1:
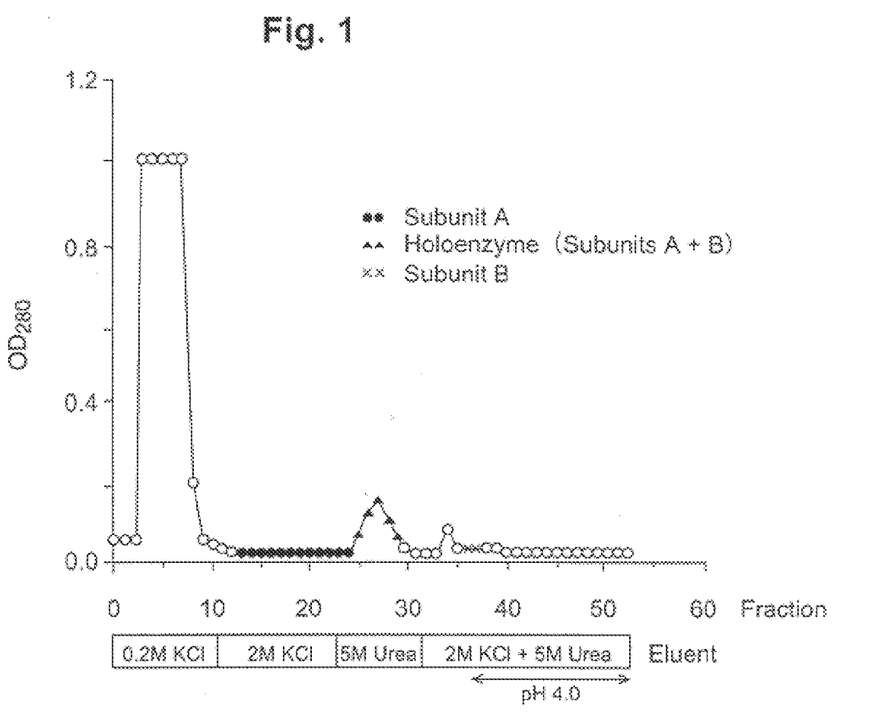
FIG. 1 is a drawing showing an elution pattern of DNA gyrase in novobiocin-Sepharose column chromatography.

The fractions whose activity had been found were collected as a fraction containing the holoenzyme of DNA gyrase (complex of subunits A and B). Part of fractions other than the active fractions was taken and a diluted active fraction was added thereto to assay as to whether the supercoiling activity was recovered or not. The fractions whose supercoiling activity was recovered were collected as roughly purified subunit A fractions. Next, part of this subunit A fraction was added to the other fractions to assay as to whether the supercoiling activity was recovered or not. The fractions whose activity was recovered were collected as roughly purified subunit B fractions. The elution pattern of proteins from the novobiocin-Sepharose column is shown in FIG. 1. DNA gyrase holoenzyme (complex of subunits A and B), subunit A and subunit B were found in fractions eluted with 5M urea, fractions eluted with 2M KCl and fractions eluted with 2M KCl+5M urea, respectively.

(3) Purification of Subunits A and B of *Escherichia coli* DNA Gyrase

Purification of subunits A and B was carried out as follows. 85 ml of the roughly purified subunit A fraction (diluted with a TED buffer five times) obtained in the above (2) was loaded on a heparin-Sepharose CL-6B (available from Pharmacia Co.) column (bed volume 15 ml) which had been equilibrated with a 10% glycerin-containing TED buffer. After washing with the same buffer, it was eluted with 10% glycerin-containing TED buffers which contain 0.05M KCl, 0.2M KCl, 2M KCl, 2M KCl-5M urea and 2M KCl-5M urea (pH 4.0), respectively, and fractionated. Each fraction (about 5 μl) added with the holoenzyme fraction (about 2.5 μl) obtained in the above (2) was measured for the supercoiling activity and purified subunit A-containing fractions were determined.

35 ml of subunit B fraction (diluted with TED buffer five times) obtained in the above (2) was loaded on a novobiocin-Sepharose column (bed volume 10 ml) which had been equilibrated with a 10% glycerin-containing TED buffer. After washing with the same buffer, it was eluted with 10% glycerin-containing TED buffers which contain 2M KCl, 2.5M urea, 5M urea, 2M KCl-5M urea and 2M KCl-5M urea (pH4.0), respectively, and fractionated. Each fraction to which the purified subunit A fraction was added was measured for the supercoiling activity and purified subunit B fractions were determined. Each of the purified subunit fractions was dialyzed using a 50% glycerin-containing TED buffer and preserved at −20° C.

(4) Isolation of *Escherchia coli* DNA Gyrase-inhibiting Protein

Figure 2:
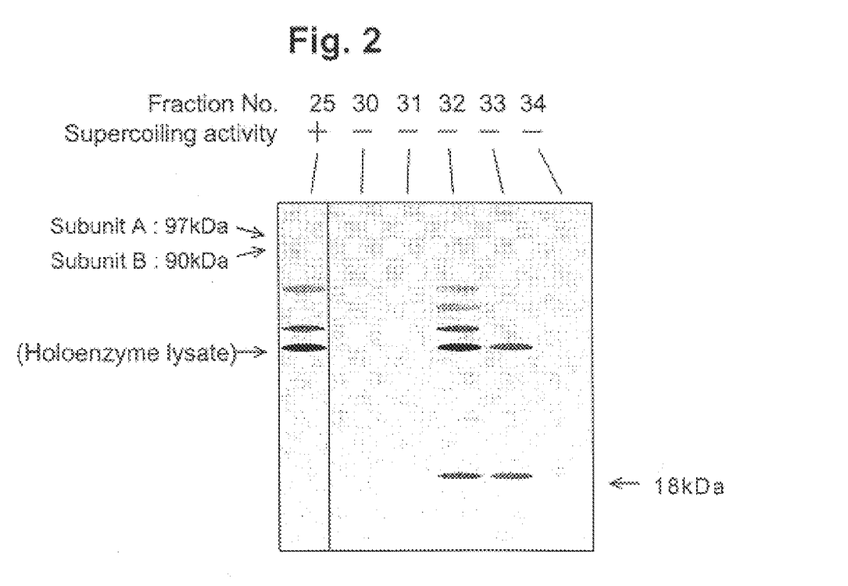
FIG. 2 is a drawing of SDS-polyacrylamide gel electrophoresis of fractions obtained by novobiocin-Sepharose column chromatography.

All the fractions obtained by the novobiocin-Sepharose column chromatography in the above (2) were subjected to SDS-polyacrylamide gel electrophoresis (SDS-PAGE) to compare the electrophoresis patterns of active and inactive fractions. As a result, Fraction Nos. 32 and 33 had an electrophoresis image corresponding to the holoenzyme while they showed no supercoiling activity, and they were recognized to have the band of 18 kDa protein in common (FIG. 2).

Fraction No. 32 (0.4 ml) was loaded on a Sephadex G-75 (column volume 3.5 ml) which had been equilibrated with a 10% glycerol-containing TED buffer and gel filtration was carried out. After fractionation by elution with a TED buffer, part of each fraction was taken and subjected to SDS-polyacrylamide electrophoresis to confirm the band of 18 kDa protein, and the protein in fractions wherein the 18 kDa protein, i.e. the DNA gyrase-inhibiting protein (DGI) became a single band, was collected as purified DGI. As a result, about 1.5 μg of purified DGI was obtained from 26.5 g of the wet bacterial cells.

(5) DNA Gyrase-inhibiting Activity of DGI

Figure 3:
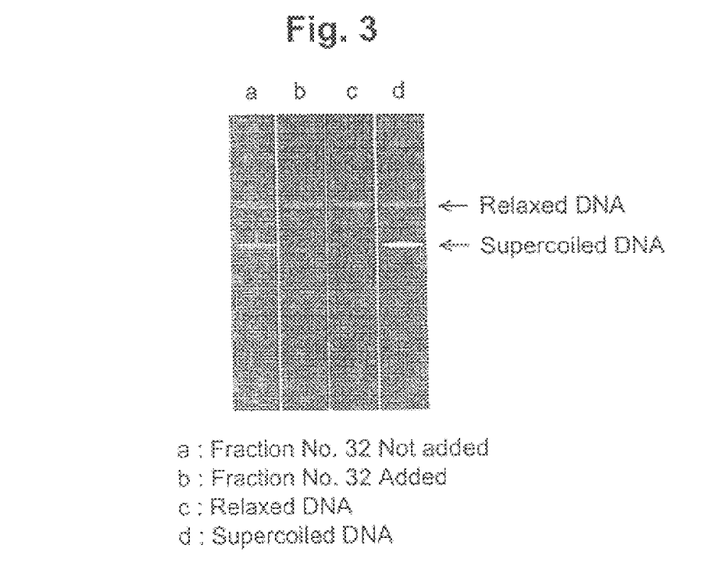
FIG. 3 is a drawing of agarose gel electrophoresis showing the disappearance of DNA gyrase activity by Fraction No. 32.

No. 32 fraction (5 μl) was added to the measurement system for the supercoiling activity of DNA gyrase described in the below-mentioned Reference Examples, i.e. a reaction liquid (15 μl) containing relaxed pBR322 DNA (0.1 μg), subunit A (1 U) and subunit B (1 U). Reacted therewith, the relaxed plasmid DNA was not converted into the supercoiling form (FIG. 3). From this, it was confirmed that No. 32 fraction contained an inhibitor to the supercoiling activity of DNA gyrase. It was also confirmed that the purified DGI obtained in the above (4) perfectly inhibited the supercoiling activity of DNA gyrase at a concentration of 8 μg/ml.

(6) Determination of N-terminal Amino Acid Sequence of DGI Derived from *Escherchia coli*

The N-terminal amino acid sequence of the purified DGI obtained in the above (4) was determined using Peptide Sequencer LF3400 (available from Beckman Co.). The thus obtained amino acid sequence of N-terminal 16 residues was represented by Sequence ID NO:1 in Sequence Listing mentioned hereinafter.

Example 2

Cloning of *Escherichia coli* dgi Gene and Determination of Base Sequence Thereof Using a nucleic acid sequence data bank (EMBL/Genbank/DDBJ), homology search was carried out for the N-terminal amino acid sequence of *Escherichia coli* DGI determined in the above-mentioned Item (6) of Example 1, and thereby it was found that the N-terminal sequence of DGI was identical with the N-terminal amino acid sequence of a product YeeB assumed to exist in the sbcB region (EMBL Accession No. U00009) of *Escherichia coli* K-12 strain chromosomal DNA. The molecular weight of YeeB estimated from the sequence was 18,081 Dalton and it was identical with the molecular weight of DGI. From these, it was believed that the assumed YeeB was DGI and the DGI-encoding gene (dgi gene) was present in a portion containing a translation region of yeeB gene.

Thus, a region corresponding to the 189th–1370th bases from the 5'-end of the above-mentioned sbcB region (EMBL Accession No. U00009) was cloned from *E, coli* KL16 strain chromosomal DNA by polymerase chain reaction (PCR) as mentioned below. Oligonucleotide primers wherein BamHI recognition sites were incorporated into the both ends of a concerned sequence were designed and synthesized with a DNA synthesizer (the sequence of the sense primer being shown in Sequence ID NO:2 and the sequence of the antisense primer in Sequence ID NO:3 of the below mentioned Sequence Listing, respectively). The PCR reaction was carried out in a PCR buffer (composition: 50 mM KCl, 10 mM Tris-HCl (pH 9.0) and 1% Triton X-100) added with 0.5 mg/ml *E. coli* KL16 chromosomal DNA, 800 μM dNTP mixture, 0.66 μM the sense primer, 1 μM the antisense primer, 2 mM $MgCl_2$ and 0.025 U/μl Taq polymerase (30 cycles of 2 minutes at 94° C., 2 minutes at 51° C. and 3 minutes at 72° C.) to amplify DNA. The 1.2 kbp DNA fragment obtained by the PCR was cleaved with a suitable restriction enzyme and ligated to a vector plasmid pUC19 (available from Takara Shuzo Co.), and the thus obtained recombinant plasmid was introduced into *E. coli* JM109 strain. These recombinant plasmids were used to determine the base sequence of the 1.2 kbp DNA fragment by the dideoxy method with a fluorescent DNA sequencer (available from Hitachi Co.). The thus obtained base sequence and the amino acid sequence of a protein encoded by an open reading frame therein were shown in Sequence ID NO:6. The sequence was identical with the sequence (yeeB gene) in the sbcB region (EMBL Accession No. U00009) of *E. coli* K-12 which was already registered at a DNA base sequence data bank. Further, the N-terminal amino acid sequence of protein encoded by the open reading frame was identical with the N-terminal sequence of DGI and it was believed that the DNA and amino acid sequences represented by Sequence ID NO:6 were the DNA sequence of dgi gene of *E. coli* and the amino acid sequence of DGI.

Example 3

DGI Genes of Various Bacterial Chromosomes

DGI was important to bacterial growth and presumed to be present universally. Thus, southern hybridization with various bacterial chromosomal DNAs was performed using a DNA fragment of the dgi gene obtained in the above Example 2.

Southern hybridization was carried out in accordance with the method described in Molecular Cloning (vol. 2, 6.2–6.19 and 9.31–9.46, 1989). Chromosomes derived from various bacteria were used which was prepared by the conventional method and then digested with EcoRI. As a probe was used an NdeI-cleaved fragment which was in the gene derived from *E. coli* cloned in the above (6) of Example 2 and was labeled with $^{32}P$. Hybridization was carried out under normal stringent conditions. That is, after shaking for 4 hours at 42° C. in a pre-hybridization solution (5×SSPE, 5×Denhardt's solution, 0.5% SDS and 50% formamide) containing SSPE (180 mM NaCl, 1 mM EDTA and 10 mM sodium phosphate (pH 7.7)), a labeled probe was added, and, hybridization was carried out at 42° C. for 14 hours, and washing was performed under the following three conditions:

Washing condition 1: 0.1% SDS, 0.1% SSPE, 65° C.
Washing condition 2: 0.1% SDS, 0.1% SSPE, 52° C.
Washing condition 3: 0.1% SDS, 1×SSPE, 52° C.

The strength of hybridization was assessed as follows:

+++: Clear hybridization band in autoradiography after washing under the washing condition 1
++: Clear hybridization band in autoradiography after washing under the washing condition 2
+: Clear hybridization band in autoradiography after washing under the washing condition 3

The results thereof were shown in Table 1 below.

TABLE 1

| Strain Name | Hybridization Strength |
|---|---|
| Escherichia coli K-12 | +++ |
| Escherichia coli ML1410 | +++ |
| Escherichia coli ATCC25922 | +++ |
| Escherichia coli NIHJ JC-2 | +++ |
| Shigella boydii IID627 | +++ |
| Shigella dysenteriae IID633 | +++ |
| Shigella sonnei TRRL10805 | +++ |
| Citrobacter freundii IID976 | ++ |
| Pseudomonas aeruginosa ATCC27853 | + |
| Bacillus subtilis ATCC6633 | + |
| Enterococcus faecalis ATCC29212 | + |
| Staphylococcus aureus RN450 | + |

+++ Strong hybridization
++ Medium hybridization
+ Slightly weak hybridization

As shown in Table 1, there were found fragments which hybridized under stringent conditions with the fragment of dgi gene (the NdeI fragment corresponding to the 225th–815th bases of Sequence ID NO:6) derived from *Escherichia coli*, in microorganisms of Shigella genus, Citrobacter genus, Pseudomonas genus, Bacillus genus, Enterococcus genus and Staphylococcus genus.

It was considered that there were present homologous dgi genes in these microorganisms and that especially genes from Shigella genus and Citrobacter genus had extremely high homology with those from Escherichia genus. Homologous genes were distributed in many kinds of microorganisms, like this, and thereby it would be suggested that DGI is important to bacterial growth.

Example 4

Large Amount Expression of *E. coli* dgi by Gene Recombination and Purification Thereof (1) Preparation of Vector for DGI Expression In order to prepare large amounts of DGI protein, a DGI expression system was constructed using vector plasmid pLEX (available from Invitrogen Co.) for protein expression as follows. The system of the expression vector pLEX is to control expression of a concerned gene by transcriptional regulation with tryptophan as an inducer. That is, when tryptophan was absent, cI repressor protein was expressed from λ1gene under trp promoter and bound to the operator region of PL promoter on the vector to repress the transcription of the concerned gene ligated to the downstream of PL promoter. On the other hand, if tryptophan was present, there was formed a tryptophan-repressor complex, which was tightly bound to trp operator to inhibit expression of cI repressor protein, and thereby cI repressor was dissociated from PL promoter to start transcription of the concerned gene.

As a fragment to be incorporated into the plasmid pLEX, a fragment in which the restriction enzyme NdeI-recognizing sites were added to the both ends of dgi gene region (a fragment corresponding to the 255th–815th bases of Sequence ID NO:6) whose base sequence was determined in Example 2 above was prepared by PCR. *E. coli* KL 16 strain chromosomal DNA was used as a template DNA for PCR and primers were synthesized using a DNA synthesizer. (The sequences of the sense primer was shown by Sequence ID NO:4 and the sequence of the antisense primer was shown by Sequence ID NO:5.) The thus obtained PCR product was ligated to a vector plasmid pT7BlueT (available from Novagen Co.) and introduced into *E. coli* JM109 to prepare a recombinant plasmid. The resulted recombinant plasmid was cleaved with NdeI and separated by agarose electrophoresis, and thereafter an NdeI fragment of 473 bp was purified from the gel, and was ligated to pLEX. It was introduced into *E. coli* GI724 (Invitrogen Co, USA) by the electroporation method to prepare a recombinant plasmid and the insertion direction of insertion fragment was decided by the cleavage pattern with EcoRV. Recombinant plasmid pCA17 was obtained wherein the insertion fragment containing the dgi gene was inserted in correct direction (sense direction). Electroporation was carried out using Electrocell Manipulator 600 (available from BM Kiki K. K.) under the conditions of potential difference 2.25 kV and electrical resistance 129Ω. GI724 strain transformed by recombinant plasmid pCA17 wherein the insertion fragment containing the dgi gene was inserted into vector plasmid pLEX in positive direction, i.e. *E. coli* GI724 (pCA17) strain, has been deposited at National Institute of Bioscience and Human-Technology (NIBH) (1-3, Higashi 1-chome, Tsukuba-shi, Ibaraki-Ken Japan) under Accession No. FERM BP-6133 on Oct. 6, 1997.

(2) Large Amount Expression of *E. coli* DGI

Figure 4:
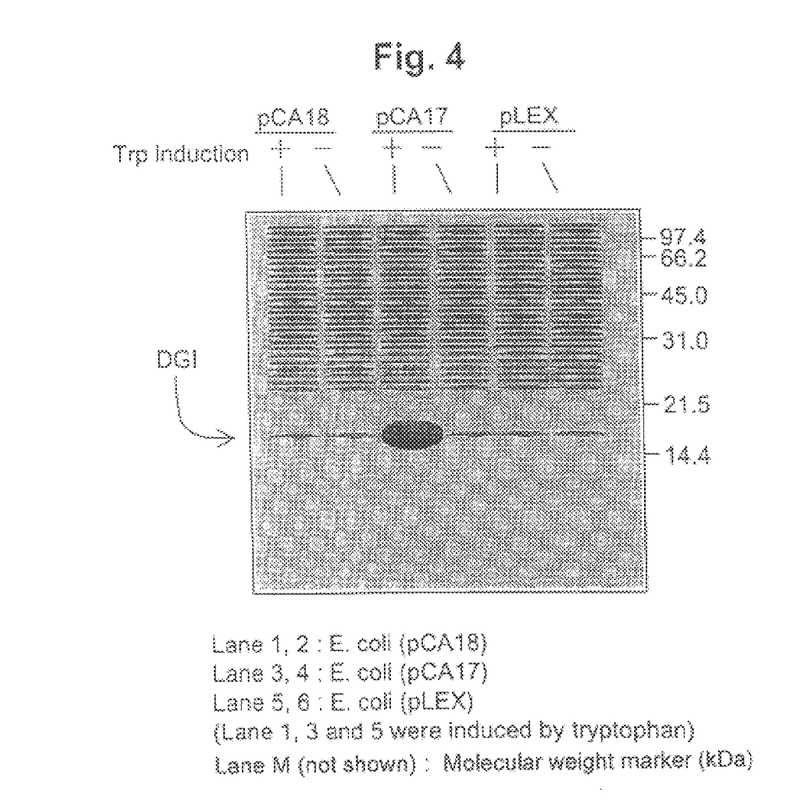
FIG. 4 is a drawing of SDS-polyacrylamide gel electrophoresis showing the expression in great amounts of DGI in *Escherichia coli*.

*E. coli* GI724 (pCA17) strain obtained in the previous item (1) was subjected to shake culture in RM medium containing 100 μg/ml of ampicillin (42 mM $Na_2HPO_4$, 22 mM $KH_2PO_4$, 8.5 mM NaCl, 18 mM $NH_4Cl$ (pH7.4), 2% Casamino acid, 1% glycerol and 1 mM $MgCl_2$). When the $OD_{600}$ value reached at about 0.5, tryptophan was added to a final concentration of 100 μg/ml and thereby the expression of DGI protein was induced. Thereafter, shake culture was continued for 5 hours at 37° C. One ml of the culture broth was taken and centrifuged to collect the bacterial cells. The thus obtained cells were dissolved in 100 μl of SDS buffer (50 mM Tris-HCl (pH 6.8), 138 mM SDS, 1.5M glycerin and 280 mM 2-mercaptoethanol) and was subjected to bacteriolysis by heating for 5 minutes at 95° C. and then preserved in ice. 20 μl of the supernatant was tested for protein expression by SDS-polyacrylamide gel electrophoresis (SDS-PAGE). As a result (FIG. 4), it was found that the strains transformed by pCA17 expressed large amounts of an about 18 kDa protein corresponding to DGI. On the other hand, in the strains transformed by recombinant plasmid pCA18 wherein the dgi gene-containing insertion fragments were inserted in reverse direction (antisense direction) or the strains transformed by vector pLEX, large amount expression was not found. When strains which expressed a large amount of DGI were observed with microscope, they were lank and elongated and it was believed to be abnormal in its cell division. From this, it is considered that medical agents which enhance the activity and/or expression of DGI are useful as antimicrobial agents.

(3) Purification of E. coli DGI

In the same manner as in the above (2), E. coli GI724 (pCA17) strain was cultured and subjected to expression induction with tryptophan. Bacterial cells obtained by centrifugation were suspended in 10 ml of Solution A (30 mM Tris-HCl (pH 7.5) and 30 mM NaCl) and ultrasonically pulverized in ice. After pulverization, centrifugation (at 40° C., 8000 rpm for 20 minutes) was carried out and thus obtained supernatant was subjected to ammonium sulfate precipitation with 60% saturation followed by further centrifugation at 17000×G for 20 minutes. The obtained pellets were dissolved in 30 ml of a TED solution (10 mM Tris-HCl (pH 7.5), 1 mM EDTA and 1 mM DTT) and dialyzed with the same solution. After dialysis, it was loaded to Q-Sepharose fast flow column (0.55 $cm^2$ ×9 cm) (available from Pharmacia Co.) which had been equilibrated with a TED solution and subjected to linear concentration gradient (from 0.025M to 0.8M) of NaCl and elution and fractionation for protein were carried out with 140 ml of a TED solution (linear velocity 150cm/hr). Each fraction was subjected to SDS-PAGE and fractions in which the 18 kDa protein band was confirmed were collected. The collected fractions were fractionated by gel filtration using TSK gel Toyopearl HW-55 (2.25$cm^2$ ×32cm)(available from Toso Co.) which had been equilibrated with a TED solution and fractions in which the 18 kDa protein band was confirmed were centrifugally concentrated to 200 µl. After the concentrate was subjected to SDS-PAGE, the concerned DGI protein was extracted from the gel and subjected to gel filtration again with TSK gel Toyopearl HW-55 to obtain purified DGI (600 µg). The amount of the protein was calculated from the absorbance measurement at 595 nm using a solution of Coomassie Brilliant Blue dye for protein quantification.

Example 5

Measurement of DGI Activity

Figure 5:
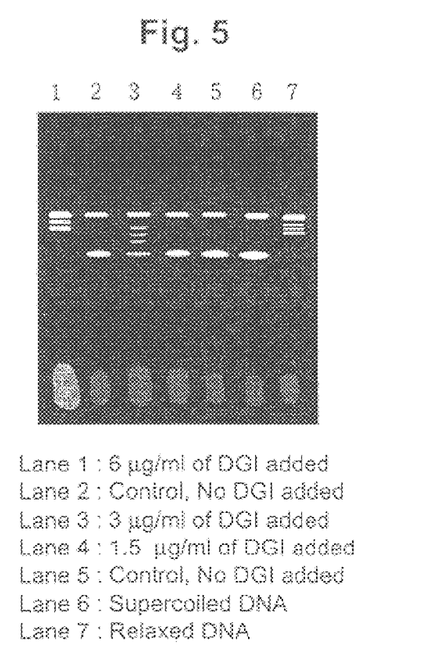
FIG. 5 is a drawing of agarose gel electrophoresis showing the inhibition action against DNA gyrase super-coiling activity by purified 18 kDa protein.

Using the purified DGI obtained in Example 4 above, DGI activity, i.e. the inhibiting activity against DNA gyrase activity (supercoiling activity), was measured. Each 5 µl of DNA gyrase subunit A (1U) and subunit B (1U) were each added to a reaction mixture for activity measurement (20 mM Tris-HCl (pH7.5), 20 mM KCl, 4 mM $MgCl_2$, 4 mM spermidine, 1.5 mM ATP, 1 mM DTT, 30 µg/ml t-RNA, 15 µg/ml BSA and 0.1 µg relaxed pBR322 DNA), and DGI (protein concentration 25, 12.5, 6.25, 3.13, 1.56, 0.78 or 0.39 µg/ml) was added thereto for the reaction for 1 hour at 37° C. After stopping the reaction by addition of 3 µl of proteinase K (1 mg/ml) while keeping the temperature at 37° C. for 30 minutes, the reaction mixture was subjected to electrophoresis with 0.8% agarose gel, dyed with a 0.5 µg/ml solution of ethidium bromide and photographed under radiation of the ultraviolet rays. The amount of super-coiled DNA was measured with a densitometer (Shimadzu-wavelength flying spot scanner CS-9000, available from Shimadzu Seisakusho Co.). The presence or absence of DNA gyrase-inhibiting activity was assayed by comparing the super-coiled DNA amounts obtained when DGI protein was added, with those obtained when no DGI protein was added. The result thereof was illustrated in FIG. 5. When DGI was added at a concentration of 6 µg/ml or more, it completely inhibited the supercoiling activity of DNA gyrase. At a concentration lower than the above concentration, the conversion to supercoiled DNA was ended in an incomplete state and a band leaving a trail from the relaxed DNA was detected.

As shown in the above, DGI activity measurement system could be constructed. In the present measurement system, when the DGI activity was compared by practicing the reaction in the presence or absence of a medical solution (or suspension), the action of medical agents to modulate (activity-enhancing action or activity-inhibiting action) can be detected, and thus screening or identification of a medical agent which modulates the DGI activity can be done.

Example 6

Measurement of Promoter Activity of E. coli dgi Gene (1) Preparation of Plasmid for Measuring Promoter Activity In the 5' upstream region of E. coli dgi gene, there is a region (yeeC gene) encoding a assumed product YeeC in the sbcB region (EMBL Accession No. U00009). Both of the genes are at a distance of about 122 bp and between these genes, there are recognized a palindrome structure which is considered to be a ρ factor-dependent terminator of yeeC, and a sequence typical in the −10 and −35 region assumed to be a promoter of dgi gene. A DNA fragment containing the promoter region of dgi gene was ligated to the lac gene to prepare a plasmid and a system capable of measuring the dgi promoter activity was constructed using β-galactosidase activity as an index.

A DNA fragment to which BamHI recognition sites were added at the both ends of a 1.2 kbp DNA fragment (a fragment corresponding to the 3rd–1184th bases of Sequence ID NO:6) containing the promoter region of dgi gene, the transcription initiation region and the 5' side of the translational region was prepared by PCR. As primers, two kinds of oligonucleotides were used which were synthesized by adding the BamHI recognition site to each of the both ends of the concerned region. As templates, the chromosomal DNA of E. coli KL16 strain was used. A fragment obtained by PCR was doubly cleaved with BamHI and RsaI to prepare a 283 bp DNA fragment comprising the assumed promoter region, the transcription initiation region and the 33 bp of the 5' end of the translational region. Vector plasmid pLGlacZ7 (Plasmid, vol. 32, pp. 233–237, 1994) was cleaved with BamHI and thereafter terminally blunted together with the previously obtained 283 bp DNA fragment, and the both were ligated to prepare a recombinant plasmid. Thus, a recombinant plasmid wherein a dgi promoter-containing fragment was ligated to the upstream of lacz gene in the same direction, i.e. plasmid pCA15 which expresses a fused protein of the N-terminal 11 amino acid residues of DGI protein and β-galactosidase, was obtained. Also, recombinant plasmid pCA16 wherein a dgi promoter-containing fragment was inserted in reverse direction was also obtained.

(2) Measurement of dgi Promoter Activity

Using a E. coli JM109 strain transformed with the recombinant plasmid pCA15 obtained in the above (1), the measurement was carried out as below. A liquid in which the above-mentioned strain was cultured for overnight was inoculated to 10 ml of an LB medium containing 50 µg/ml of kanamycin in such an amount that the $OD_{600}$ value became 0.1 and subjected to shake culture at 37° C. The culture medium was hourly measured for the turbidity at 600 nm and taken in an amount of about 0.3 to 0.5 ml. The taken culture medium was diluted such that the $OD_{600}$ value became 0.1, and then 1 ml thereof was sampled and centrifuged (14000 rpm, 1 minute) to obtain bacterial cells, which were suspended in 1 ml of a Z buffer (60 mM $Na_2HPO_4$, 40 mM $NaH_2PO_4$, 10 mM KCl, 1 mM $MgSO_4$ and 50 mM β-mercaptoethanol). After ultrasonic pulverization, it was centrifuged and the supernatant was taken in an amount of 600 μl as a sample solution, whose β-galactosidase activity was measured as follows. 600 μl of the sample solution was kept at 28° C. for 5 minutes, and thereafter 200 μl of a solution (4 mg/ml) of a reaction substrate ONPG (o-nitrophenyl-β-D-galactopyranoside) was added thereto, and it was kept at that temperature for 5 minutes for the reaction and the reaction was stopped by addition of 500 μl of 1M sodium carbonate. After completion of the reaction, the absorbances at 420 nm and 550 nm were measured, and the β-galactosidase activity and specific activity per μg of the protein were calculated in accordance with the method of Sambrook et al. (Molecular Cloning: A Laboratory Manual, Second Edition, Cold Spring Harbor Laboratory Press, Plainview, N.Y., 1989). The protein amounts in the sample solutions were measured using a CBB stain solution for protein quantification.

Figure 6:
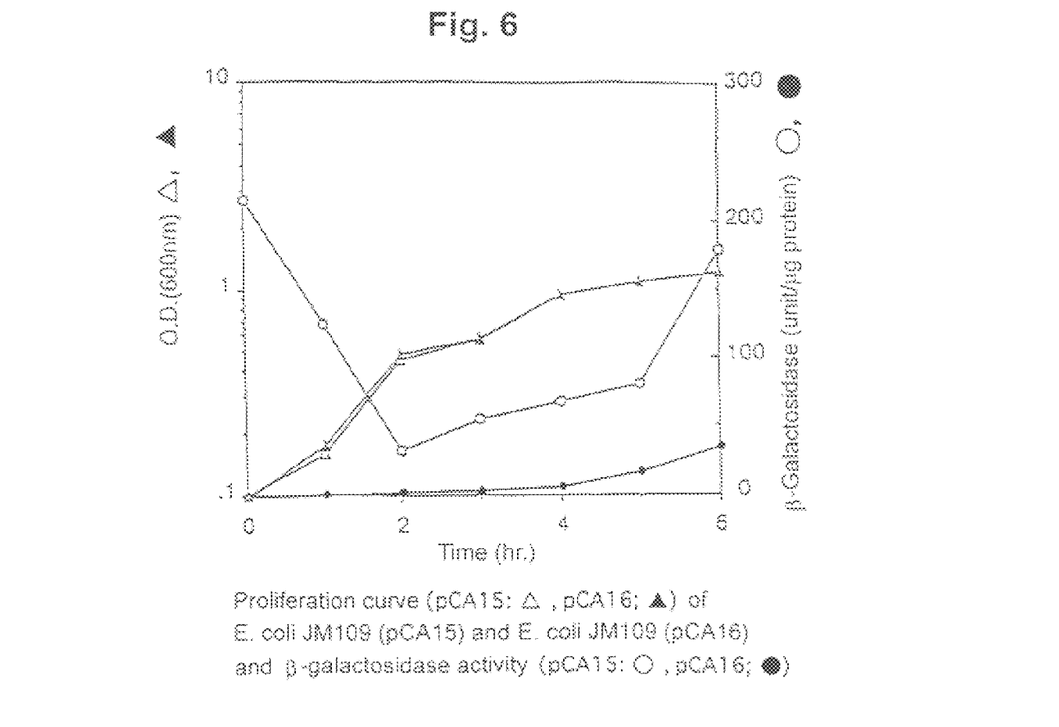
FIG. 6 is a drawing showing the change of dgi promoter activity in the propagation stage of *Escherichia coli*.

FIG. 6 showed a result of the change in dgi promoter activity with the lapse of time with growth (using expression of β-galactosidase as an index). It was found that the β-galactosidase activity per μg of the microbial protein showed the lowest value in the logarithmic growth phase ($OD_{600}$: 0.5) 2 hours after culturing while it increased until 6 hours after where the resting phase ($OD_{600}$: 1.2) was reached.

In the same manner as mentioned above, the dgi promoter activity was measured for *E. coli* JM 109 strains into which each of plasmid pCA15, pCA16 and pLGlacZ7 was introduced. As a result, the β-galactosidase activities per μg of the microbial protein 18 hours after culturing were 216, 14 and 0 units/μg, respectively. Thus, stronger expression of β-galactosidase was recognized in *E. coli* with pCA15 in comparison with the control plasmids (pCA16 and pLGlacZ7). From the fact, it was confirmed that the dgi promoter activity can be easily measured by using plasmid pCA15, with β-galactose activity as an index.

As shown in the above, the dgi promoter activity measurement system could be constructed. In this measurement system, culturing is carried out with or without addition of a solution of a medical agent (or suspension), and, by comparing the dgi promoter activities, the action of the medical agents to modulate the expression of dgi gene (expression-enhancing action or expression-inhibiting action) can be detected. Thus, screening or identification of a medical agent which modulates the DGI expression can be done.

Example 7

Expression Control of *E. coli* dgi Gene with Antisense RNA (1) Expression Control of dgi Gene by Introduction of Antisense RNA Expression Plasmid An antisense expression vector was prepared by inserting a fragment containing the translation region of dgi gene (a fragment corresponding to the 255th–728th bases of Sequence ID NO:6) into the downstream of tryptophan (trp) promoter of vector plasmid pLEX (available from Invitrogen Co.).

Figure 7:
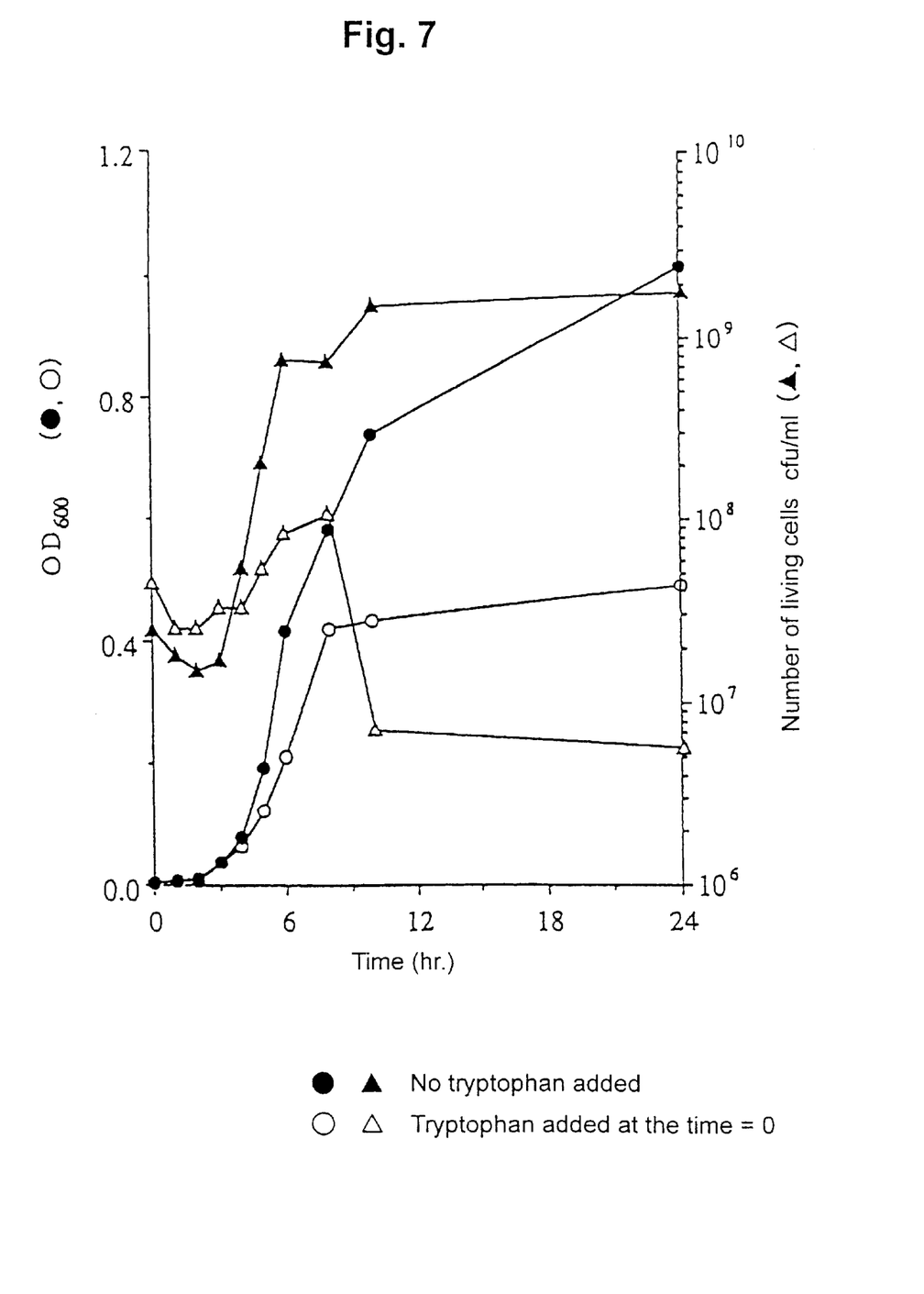
FIG. 7 is a drawing showing the effect of expression of antisense RNA of dgi gene on the growth of *Escherichia coli*.

The vector was introduced into *E. coli* GI724 strain. The antisense RNA-expressing strain thus obtained was cultured under the condition of with or without adding tryptophan, and the change with the lapse of time in the number of living cells and turbidity ($OD_{600}$) was measured. The results thereof were shown in FIG. 7. When expression induction by adding tryptophan was not carried out, the number of living cells and turbidity after 24 hours were increased up to $1\times10^9$ cfu/ml and 1.0, respectively. On the other hand, when tryptophan was added to induce expression of dgi gene antisense RNA, the number of living cells had a tendency of slight increase from $4\times10^7$ cfu/ml to $1\times10^8$ cfu/ml until 8 hours after the addition, but it was decreased to $5\times10^6$ cfu/ml after 24 hours. The $OD_{600}$ value was increased to 0.4 until 8 hours after the addition but it showed an almost constant value of 0.5 even after 24 hours. Further, elongation of the bacteria was observed in the case of antisense RNA-expressing strain. It has been reported that such abnormality in morphology was also observed when *E. coli* was treated with a new quinolone gyrase inhibitor (Takeshi Nishino et al., Chemotherapy, vol. 41(s-5), pp. 50–66, 1993). From the above result, it is considered that in *E. coli* wherein expression of dgi antisense RNA is induced, expression of dgi gene is repressed and the normal growth of bacteria is inhibited. In other words, a medical agent which inhibits the expression of dgi gene is useful as an antimicrobial agent.

Example 8

Polyclonal Antibody against *E. coli* DGI Protein (1) Preparation of Anti-DGI Antiserum 25 μg of Gerbu adjuvant (available from NACALAI TESQUE INC.) was added to 200 μl (corresponding to100 μg) of a solution of the purified DGI obtained in the above Item (4) of Example 3, and shaken for 5 minutes at room temperature to thoroughly mix them, which was subcutaneously administered to the back of a rabbit to perform primary immunization. One and 3 weeks after the primary immunization, booster immunization was carried out in the same manner. After immunization, a small amount of blood was taken from a vein of ear and its antibody titer was measured. At the time when the increase in titer of serum antibody was confirmed, about 50 ml of blood was taken from the artery of ear. The resulting blood was allowed to stand for 1 hour at 37° C. and further for overnight at 4° C., and thereafter centrifuged to obtain a serum. The obtained antiserum was, after filter filtration (pore diameter 0.45 μm), apportioned to reserve at −80° C.

(2) Purification of Anti-DGI Antibody (IgG) and Dot Blotting Assay

Using E-Z-SEP (Trade name, available from Pharmacia Co., a kit for purifying antibodies), an IgG fraction was purified from the antiserum. The IgG concentration in the purified antibody was measured in accordance with the dilution dot blotting method (Experimental protocol for anti-peptide antibodies, Shujun Sha, written by Shinobu Omi et al., pp. 73 and 74) and was found to be 300 mg/ml.

Using the dot blotting assay, the minimal amount of antigen protein, which can be recognized with the antibody, was assayed. That is, 0.5 μl of the purified DGI at a concentration of 20, 10, 5, 2.5 or 1.25 μg/ml was spotted on a nitrocellulose membrane and dried, and thereafter blocked in a 20 mg/ml BSA-containing TBS (0.15M NaCl and 20 mM Tris-HCl (pH7.5)). The membrane was immersed in the anti-DGI antigen diluted with the BSA-containing TBS (1000 times dilution), and incubated for 1 hour at 37° C. After washing the resulting membrane, it was incubated together with an anti-rabbit IgG antibody (available from Gibco. BRL Co.) labeled with horseradish peroxidase (HRP) for 0.5 hours at 37° C., and thereafter the binding of the antibody was detected by peroxidase staining using diaminobenzidine (DAB) as a substrate. As a result, it was found that the minimal protein amount of antigen (DGI) the antibody could detect is about 5 ng.

(3) Detection of E. coli DGI by Western Blotting

Figure 8:
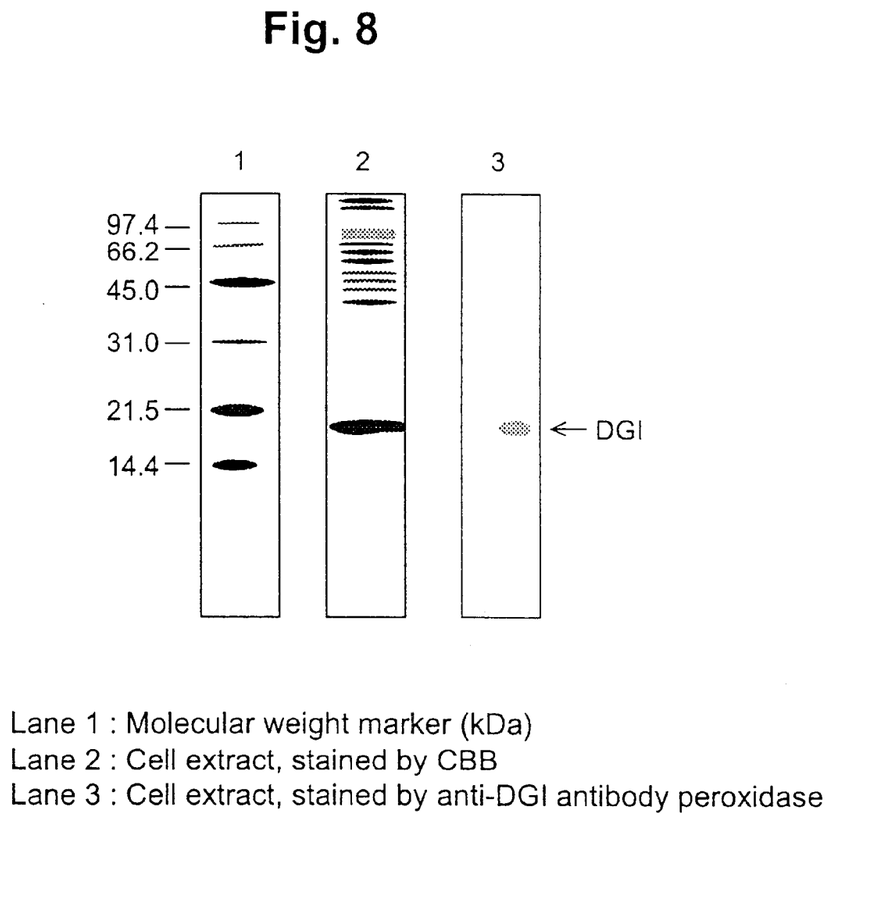
FIG. 8 is a drawing of electrophoresis showing the detection of *Escherichia coli* DGI by Western blotting using an anti-DGI antibody.

E. coli which highly expressed DGI (E. coli GI724 (pCA17) strain obtained in the above Example 4) was subjected to ultrasonic pulverization and successive certrifugation, and the resulting supernatant was separated by SDS-polyacrylamide gel electrophoresis. The gel after electrophoresis was transferred to a PVDF (polyvinylidene difluoride) membrane (available from Millipore Co.). The transferred PVDF membrane was stained with Coomassie Brilliant Blue and, after confirmation of the electrophoresis pattern of proteins, was decolorized with methanol and blocked in the 20 mg/ml BSA-containing TBS. The membrane was immersed in the anti-DGI antibody diluted with the BSA-containing TBS (1000 times dilution) for the reaction and was subjected to peroxidase staining using the HRP-labeled anti-rabbit IgG antibody and the substrate DAB, in the same manner as (2) described above. As a result, as shown in FIG. 8, a protein having a molecular weight of 18 kDa corresponding to DGI can be specifically detected. From this, it was believed that the obtained anti-DGI antibody (IgG) could be used to detect or quantify the DGI.

Reference Example

Method for Measuring Supercoiling Activity of DNA Gyrase

In accordance with the method described in Antimicrobial Agents and chemotherapy, vol. 32, pp. 104–109, 1998, the following was carried out.

0.5 µg of pBR322 DNA (the supercoiled type, available from Takara Shuzo Co.) and 1 µl of topoisomerase I (available from Takara Shuzo Co.)(6 U/µl) were added to 20 µl of a reaction liquid (35 mM Tris-HCl (pH 8.0), 72 mM KCl, 5 mM $MgCl_2$, 5 mM DTT, 5 mM spermidine and 0.01% bovine serum albumin) and reacted for 2 hours at 37° C. to prepare relaxed pBR322 DNA. 5 µl of a sample solution to be tested, 5 µl of DNA gyrase subunit A (1 U/1.25 µl) and 5 µl of subunit B (1 U/1.25 µlr) were added to 5 µl of a reaction liquid for measuring supercoiling activity (20 mM Tris-HCl (pH 7.5), 20 mM KCl, 4 mM $MgCl_2$, 4 mM spermidine, 1.5 mM ATP, 1 mM dithiothreitol, 30 µg/ml t-RNA (derived from yeast) and 15 µg/ml bovine serum albumin) containing 0.1 µg of the relaxed pBR322 DNA, and the reaction was carried out for 1 hour at 37° C. To the mixture was added 3 µl of proteinase K (1 mg/ml) and the temperature was maintained at 37° C. for further 30 minutes to stop the reaction. The reacted liquid was subjected to electrophoresis with 0.8% agarose gel electrophoresis (electrophoresis buffer TAE; 40 mM Tris-acetate and 1 mM EDTA) and the gel was, after staining with a 0.5 µg/ml ethidium bromide solution, photographed under the radiation of ultraviolet rays. The presence or absence of DNA gyrase inhibition was assayed by comparing the amounts of the supercoiled DNA in cases of with and without addition of a sample to be tested. As for the enzyme activity, the enzyme amount necessary to convert 50% of the amount of the relaxed plasmid DNA into the supercoiled DNA was expressed as one unit (U).

Example 9

Cloning of dgi Gene of Shigella Genus Microorganism

As shown in the above Example 3, it was found that an EcoRI fragment which strongly hybridizes with the dgi gene of E. coli is recognized in the chromosome of Shigella genus, and that the size of the fragment is about 7 kb. Thus, the chromosome of Shigella dysenteriae IID633 was cleaved with EcoRI and subjected to agarose electrophoresis to recover an about 7 kb DNA fragment. The obtained DNA fragment was ligated to the EcoRI-cleaved sites of pUC19 and the thus obtained recombinant plasmid was introduced into E. coli JM109 strain. Using a DNA fragment containing the dgi gene derived from E. coli as a probe, colony hybridization was carried out. As a result of the analysis of 10 strains of positive colonies, it was found that 6 strains had an EcoRI DNA fragment of 7.5 kb on the pUC19. The insertion fragment was cleaved with various restriction enzymes. As a result of analysis by the hybridization with an E. coli dgi gene-containing DNA fragment, it was believed that the dgi gene of Shigella genus was present on a 1.5 kb AvaI fragment.

In order to determine the base sequence, various deletion plasmids were prepared from plasmids containing the DNA fragment and using these plasmids the base sequence was determined by the dideoxy method with a fluorescent DNA sequencer (available from Hitachi Co., SQ5500). The sequence of 1444 bp was determined. The 1444 bp DNA base sequence of Shigella dysenteriae was compared with the sequence around E. coli dgi gene and it was found thereby that the homology as high as 98.3% was observed throughout all the area and that an open reading frame (ORF) corresponding to the region from the 966th base to 1169th base thereof was the ORF of dgi gene. Sequences considered as promoter and ribosome-binding regions were observed upstream the ORF while a sequence assumed ρ-independent terminator was recognized following the ORF. The DNA sequence of 1444 bp fragment containing the dgi gene derived from Shigella dysenteriae and the amino acid sequence of DGI encoded therein were illustrated in Sequence ID NO:8. The amino acid sequence of the same was also shown in Sequence ID NO:9. It was assumed that DGI of Shigella dysenteriae was a polypeptide comprising 157 amino acids and had a molecular weight of about 18 kilodaltons, similarly as in E. coli DGI. The amino acid sequences of both the DGIs had a homology as high as 96.8%.

INDUSTRIAL APPLICABILITY

The normal growth of bacteria can be inhibited by modulating the activity or expression of the DNA gyrase-inhibiting protein (DGI) of the present invention. Using the DNA gyrase-inhibiting protein (DGI) of the present invention and its gene (dgi gene), the DGI activity or the promoter activity of dgi gene can be measured and these measuring methods are useful as methods for screening and identifying a medical agent capable of modulating the DGI activity and the expression of dgi gene. The screening method and identification method are useful for developing antimicrobial agents or agricultural chemicals based on new action and mechanism. Furthermore, antisense RNA or DNA to the dgi gene is useful as a medical agent which inhibits expression of DGI, and anti-DGI antibodies can be utilized for detecting or quantifying the DGI.

What is claimed is:

1. A method for identifying a medical compound that modulates the activity of a DNA gyrase-inhibiting protein, comprising:

(a) contacting said DNA gyrase inhibiting protein to said medical compound; and (b) measuring the DNA gyrase-inhibiting activity of said protein in the presence and absence of said medical compound, wherein if in the presence of said medical compound, reduction or enhancement of DNA gyrase-inhibition occurs, but in the absence of said medical compound, reduction or enhancement of DNA gyrase-inhibition does not occur, then said medical compound modulates the activity of said DNA gyrase-inhibiting protein; and (c) selecting or identifying a medical compound that modulates the activity of a DNA gyrase-inhibiting protein; and wherein said DNA gyrase-inhibiting protein is a protein encoded by a DNA, the complement thereof which hybridizes with a DNA fragment comprising the base sequence represented by SEQ ID NO:6 or SEQ ID NO:8 under stringent conditions.

2. A method for identifying a medical compound that modulates the activity of a DNA gyrase-inhibiting protein, comprising:

(a) contacting said DNA gyrase inhibiting protein to said medical compound; and (b) measuring the DNA gyrase-inhibiting activity of said protein in the presence and absence of said medical compound, wherein if in the presence of said medical compound, reduction or enhancement of DNA gyrase-inhibition occurs, but in the absence of said medical compound, reduction or enhancement of DNA gyrase-inhibition does not occur, then said medical compound modulates the activity of said DNA gyrase-inhibiting protein; and (c) selecting or identifying a medical compound that modulates the activity of a DNA gyrase-inhibiting protein; and wherein said DNA gyrase-inhibiting protein is a protein encoded by a DNA comprising the base sequence represented by SEQ ID NO:6 or SEQ ID NO:8.

3. A method for identifying a medical compound that modulates the activity of a DNA gyrase-inhibiting protein, comprising:

(a) contacting said DNA gyrase inhibiting protein to said medical compound; and (b) measuring the DNA gyrase-inhibiting activity of said protein in the presence and absence of said medical compound, wherein if in the presence of said medical compound, reduction or enhancement of DNA gyrase-inhibition occurs, but in the absence of said medical compound, reduction or enhancement of DNA gyrase-inhibition does not occur, then said medical compound modulates the activity of said DNA gyrase-inhibiting protein; and (c) selecting or identifying a medical compound that modulates the activity of a DNA gyrase-inhibiting protein; and wherein said DNA gyrase-inhibiting protein is a protein comprising either (1) the amino acid sequence represented by SEQ ID NO:7 or (2) the amino acid sequence represented by SEQ ID NO:9.

4. The method of claim 1, 2, or 3, wherein the DNA gyrase-inhibiting protein is derived from a microorganism belonging to Escherichia genus.

5. The method of claim 1, 2, or 3, wherein the DNA gyrase-inhibiting protein is derived from a microorganism belonging to Shigella genus.

6. The method of claim 1, wherein the DNA gyrase-inhibiting protein is derived from a microorganism belonging to Citrobacter genus, Pseudomonas genus, Bacillus genus, Enterococcus genus or Staphylococcus genus.

7. The method of claim 1, 2, or 3, wherein the medical compound is an antimicrobial agent.

* * * * *